United States Patent [19]

Ullman et al.

[11] 4,056,608

[45] Nov. 1, 1977

[54] CARDIAC GLYCOSIDE OR AGLYCONE ASSAYS

[75] Inventors: Edwin F. Ullman, Atherton; Joyce Y. Chang, Sunnyvale; Kenneth G. McNeil, Santa Clara, all of Calif.

[73] Assignee: Syva Company, Palo Alto, Calif.

[21] Appl. No.: 674,782

[22] Filed: Apr. 8, 1976

[51] Int. Cl.² .................... G01N 33/00; G21H 5/02
[52] U.S. Cl. .................... 424/1; 23/230 B; 424/12
[58] Field of Search .............. 424/1, 12; 23/230 B; 195/103.5

[56] References Cited

U.S. PATENT DOCUMENTS

| | | | |
|---|---|---|---|
| 3,855,208 | 12/1974 | Rutner et al. | 424/1 X |
| 3,925,355 | 12/1975 | Piasio et al. | 424/1 X |
| 3,933,997 | 1/1976 | Hersh et al. | 424/1 |
| 3,975,511 | 8/1976 | Vann et al. | 424/1.5 |

OTHER PUBLICATIONS

Wong, Clinical Chemistry, vol. 21, No. 2, 1975, pp. 216–220.
Oliver et al., Journal of Clinical Investigation, vol. 47, No. 5, May, 1968, pp. 1035–1042.

*Primary Examiner*—Benjamin R. Padgett
*Assistant Examiner*—Christine M. Nucker
*Attorney, Agent, or Firm*—Townsend and Townsend

[57] ABSTRACT

Immunoassays for digoxin and its congeners are provided by pre-treating the serum sample with dilute aqueous alkaline solutions under mild conditions and for short periods of time, preferably in combination with a chelating agent, prior to carrying out the immunoassay. The method finds particular application with radioimmunoassays and homogeneous enzyme immunoassays.

9 Claims, No Drawings

CARDIAC GLYCOSIDE OR AGLYCONE ASSAYS

BACKGROUND OF THE INVENTION

1. Field of the Invention

Immunoassays find wide application for the determination of a variety of drugs. Critical to the immunoassay is the reproducible binding of an antibody to the drug (hapten) of interest. Because of the nature of immunoassays, there can be a wide variety of interferences or sources of error. Where the sample is a serum sample, the serum brings with it all of the endogenous proteinaceous and polysaccharidic compositions present in serum, as well as numerous other organic compounds which are in the blood stream, either naturally or due to ingestion by the patient. These various materials can become involved, so as to interfere with the reproduceability and accuracy of the immunoassay.

The materials of usual interest, and for the purposes of the present invention, digoxin and digitoxin, are normally present in serum at extremely low concentrations, generally less than about $10^{-8}$M. Since in carrying out the immunoassay, the serum sample will be subjected to dilution, the concentration of the digoxin in the assay sample will generally be less than $10^{-9}$M. Thus, any significant interaction between the digoxin and digitoxin and the materials present in the serum or the antibody with the materials present in the serum can lead to erroneous results.

In attempting to enhance the accuracy and reproduceability of the immunoassay, methods must be chosen which do not introduce extraneous materials which will interfere subsequently with the assay. Furthermore, any material which is introduced must not affect the cardiac glycoside, so as to modify its binding to the antibody adversely. In addition, depending upon the particular immunoassay employed and the indicator used for detection, the method must not affect the indicator or the method for measurement in an adverse manner.

2. Description of the Prior Art

In Wong, Clin. Chen. 21, 216 (1975), an alkaline solution is employed for pre-treatment of serum in a competitive protein-binding procedure for determining serum thyroxine.

SUMMARY OF THE INVENTION

Serum, to be analyzed by an immunoassay for cardiac glycoside or aglycone is combined with a dilute aqueous alkaline solution, particularly an alkali metal hydroxide solution, preferably in combination with a chelating agent, at a moderate temperature for a short period of time. The resulting solution is then diluted with buffer or neutralized to the desired pH and the necessary reagents added. The cardiac glycoside or aglycones are then determined according to conventional immunoassay techniques, particularly radioimmunoassay and homogeneous enzyme immunoassay.

DESCRIPTION OF THE SPECIFIC EMBODIMENTS

An improved method for determining digoxin or its congeners e.g. digitoxin, digitoxigen, digoxigenin, digitoxigenin, etc. by immunoassays is provided, enhancing the accuracy and reproduceability of the immunoassay. The improvement comprises combining a serum sample with a small amount of a dilute alkaline solution at moderate temperatures for relatively short periods of time, preferably in combination with an amino (poly[aklylene carboxylic acid]) chelating agent. The resulting solution is then empolyed in a substantially conventional manner in an immunoassay.

In accordance with the subject invention, a serum sample is combined in a volume ratio generally varying from about 0.1–10:1, more usually 0.5–2:1 with an aqueous alkaline solution, so as to provide a final solution having a pH of at least about 10.5, generally in the range of about 11 to 13. The alkaline solution will generally vary from about 0.01 to 5N, more usually 0.1 to 2N in an alkali metal hydroxide, particularly of atomic number 11 to 19 and more particularly, sodium hydroxide.

The solutions are combined and incubated at a temperature of at least about 15° C and not exceeding about 50° C, more usually from about 20° to 40° C and preferably from about 25° to 30° C. The incubation time will be a function of the pH and temperature and will generally be at least about 1 minute, more usually at least about 5 minutes and not more than about 1 hour, preferably not more than about 30 minutes.

At the end of the incubation period, either sufficient buffer is added to provide the desired pH, or the solution may be neutralized with a mineral acid e.g. hydrochloric acid to reduce the pH, prior to the addition of buffer for the immunoassay.

The buffered solution or solution having a pH at the pH desired for the assay is now ready for testing. In the homogeneous enzyme immunoassay, reagents are added which include an enzyme conjugate to a digoxin derivative or a digoxin congener derivative, substrates for the enzyme, and antibody for digoxin or its congener (antidigoxin). A description of a particular homogeneous enzyme immunoassay for digoxin may be found in co-pending Application Ser. No. 649,942, filed 01/19/76 (TOWNSEND and TOWNSEND Docket No. 3652-36-13).

While satisfactory results can be obtained where the time intervals for the various procedural steps are maintained fairly constant, particularly the time interval for the pretreatment time, where the pretreatment time varies significantly, results can be erratic. However, by including in the pretreatment medium a small amount of a chelating agent, particularly aminoalkylenecarboxylic acids of from 1 to 3 amino nitrogen atoms and alkylene groups of from 1 to 2 carbon atoms, consistent results can be obtained despite varying pretreatment times. The concentration of the chelating agent will generally be at least 0.01M and not exceed 0.5M, more usually in the range of 0.02 to 0.1M, preferably about 0.05M. Of particular interest is ethylene diamine tetracetic acid, normally employed as the sodium salt.

In carrying out the assay, the serum solution which has been treated with the alkaline solution is combined with a reagent solution which contains antibody for digoxin, 0.08M NAD, 0.13M G-6-P, 1% w/v rabbit serum albumin, 0.05% w/v sodium azide, 0.005% w/v Thimerosal, buffered with 0.055M tris-HCl pH 7.9 (30° C). (w/v intends grams per 100ml.) The solution is then incubated, followed by the addition of the enzyme conjugate which is at a concentration to provide a convenient change in the spectrophotometric reading at 340nm at 30° C. Included in the enzyme solution is 1% w/v rabbit serum albumin and 0.9% w/v sodium chloride.

Upon addition of the enzyme reagent, a stop watch is begun, the mixture agitated, and a reading taken within 1 minute from the time of the addition of the enzyme reagent. The mixture is the allowed to sit in a thermostatted bath at 30° C for an additional 30 minutes and a second reading taken. The readings are recorded in $\Delta$OD/min. and by employing appropriate standards, one can derive a concentration versus $\Delta$OD/min. curve for determining the concentration of digoxin.

Radioimmunoassays for digoxin are commercially available and may be purchased as kits. In carrying out the radioimmunoassay, the reagent employed is a tagged digoxin, normally with either tritium or iodine-125. The alkaline treated serum solution is combined with antibody and tagged digoxin, a reagent is added to precipitate the antibody, the mixture centrifuged and the supernatant solution analyzed for radioactivity. By employing appropriate standards, a ratioactivity versus digoxin concentration curve can be established.

To demonstrate the effectiveness of employing the alkaline pre-treatment, a number of experiments were carried out.

In the first study, twenty different sera were employed, which were free of digoxin. In one series of experiments the sera were employed with antibody present in the assay mixture and with another series with the same sera, there was no antibody, so as to provide the maximum enzyme rate. It should be understood, that binding of antibody to the enzyme-digoxin conjugate results in a reduction in rate.

The particular enzyme conjugate employed in these tests was glucose-6 phosphate dehydrogenase. The specific protocol was to add to a cuvette 100$\mu$l of serum and 100$\mu$l of 0.1N sodium hydroxide and incubate the mixture for 15 minutes at 30° C. To the mixture is then added 500$\mu$l of the assay buffer (the buffer described for the antibody reagent), the mixture is agitated and 100$\mu$l of the substrate solution in buffer is added followed by 50$\mu$l of the antibody solution (or equivalent amount of buffer) with 400$\mu$l of buffer. Finally, 50$\mu$l of the enzyme solution and 400$\mu$l of buffer are added and the enzyme rate measured. The following table indicates the results for the 20 serum samples containing no digoxin.

TABLE I

|  | Antibody | No Antibody |
|---|---|---|
| $\bar{x}$ | 425.90 | 561.4 |
| $\sigma$ | 3.70 | 3.6 |
| C.V. | 0.87 | 0.64 |

Following the procedure described above (no digoxin present), except that less buffer was used so as to provide a final volume of 1.2ml, no antibody was included and 5 100$\mu$l aliquots of a common serum pool were diluted with 100$\mu$l of water and another 5 100$\mu$l aliquots of serum were diluted with 100$\mu$l of 0.1N sodium hydroxide and the diluted serum samples incubated for 15 minutes at 30° C. The following table is a comparison of the results for the enzyme rate with and without alkaline treatment.

TABLE II

|  | With Treatment | Without Treatment |
|---|---|---|
| $\bar{x}$ | 539 | 422 |
| $\sigma$ | 2.5 | 20.9 |
| C.V. | 0.46 | 4.95 |

In the next study, various incubation times were employed, whereby 200$\mu$l of serum containing 1 ng/ml digoxin was treated with 50$\mu$l of 0.5N sodium hydroxide. Otherwise, the procedure followed that described above. The following table indicates the results.

TABLE III *

| Incubation Time Min. | $\bar{x}$ | $\sigma$ | C.V. |
|---|---|---|---|
| 0 | 601 | 13.9 | 2.91 |
| 5 | 692 | 4.7 | .68 |
| 15 | 691 | 6.0 | .87 |
| 30 | 688 | 4.4 | .64 |

* 20 serum samples

Finally, a ratioimmunoassay was employed substantially as described by Smith et al, New England J. of Medicine 281 1212 (1969). Employing 10 samples, each containing 2ug/ml of digoxin, 1ml of serum per sample was treated with 50$\mu$l of 2.1N aqueous sodium hydroxide and incubated for 15min. at ~20° C, to which was then added 100$\mu$l of an aqueous solution 0.5M $KH_2PO_4$, 0.5M $K_2HPO_4$ and 1.05M HCl. The resulting serum solution was then employed in accordance with procedures set forth for the ratioimmunoassay. The following table indicates the results.

TABLE IV *

|  | Average Assayed conc (ng/ml) | C.V. |
|---|---|---|
| w/o treatment | 1.6 | 13 |
| w/ treatment | 2.0 | 7 |

* 2 ng spike

A number of assays were carried out where the pretreatment time was varied, one series having 0.5M EDTA included and the other series without EDTA. The results are reported as $\Delta$OD for an 80 second interval between readings. (EDTA-ethylene diamine tetracetic acid, sodium salt)

| Minutes After Initial Mixing of Serum and Pretreatment Reagent | With EDTA $\Delta$OD | Without EDTA $\Delta$OD |
|---|---|---|
| 2 | 607 | 593 |
| 4 |  | 586 |
| 5 | 611 |  |
| 6 |  | 585 |
| 9 | 618 |  |
| 10 |  | 572 |
| 11 | 607 |  |
| 14 |  | 537 |
| 15 | 615 |  |
| 16 |  | 541 |
| 21 |  | 503 |
| 26 | 610 |  |

It is evident from the above results, that greater reproduceability and accuracy in immunoassays is achieved by a mild pre-treatment of serum suspected of containing digoxin, with an alkaline solution particularly in combination with EDTA. The pre-treatment with sodium hydroxide in no wise interferes with the subsequent immunoassay, the high pH is easily overcome by dilution with buffer and the technique employs simple reagents without requiring expensive equipment. Thus, the usefulness of immunoassays is greatly enhanced for the determination of digoxin and its congeners by the subject invention.

Although the foregoing invention has been described in some detail by way of illustration and example for purposes of clarity of understanding, it will be obvious that certain changes and modifications may be practiced within the scope of the appended claims.

What is claimed is:

1. In an immunoassay for the determination of cardiac glycosides or aglycones employing a serium sample, wherein antibody for cardiac glycosides or aglycones is employed which binds to cardiac glycosides or aglycones in competition with the indicator used for detection, the improvement which comprises:

pre-treating said serum sample with an alkaline solution under mild conditions at a pH of at least about 10.5.

2. An immunoassay according to claim 1, wherein said pH is in the range of 11 to 13, an aminoalkylene carboxylic acid chelating agent is present in said solution at a concentration in the range of about 0.01 to 0.5M. and said pretreating is at a temperature in the range of 15° to 50° C.

3. An immunoassay according to claim 2, wherein said immunoassay is a radioimmunoassay.

4. An immunoassay according to claim 2, wherein said immunoassay is an enzyme immunoassay.

5. An immunoassay according to claim 4, wherein said enzyme is glucose-6-phosphate dehydrogenase.

6. An immunoassay according to claim 1, wherein said alkaline treated solution is incubated from about 1 to 60 minutes at a temperature in the range of about 15° to 40° C.

7. An immunoassay according to claim 6, wherein the determination is for digoxin.

8. An immunoassay according to claim 6, wherein the determination is for digitoxin.

9. An immunoassay according to claim 2, wherein said chelating agent is EDTA.